United States Patent [19]

Benedictus

[11] 4,327,182

[45] Apr. 27, 1982

[54] PURIFICATION OF INFLUENZA SUB-UNIT VACCINE

[75] Inventor: Jorn D. Benedictus, Groton, Mass.

[73] Assignee: Connaught Laboratories Incorporated, Swift Water, Pa.

[21] Appl. No.: 227,240

[22] Filed: Jan. 22, 1981

[51] Int. Cl.³ .............................................. C12N 7/02
[52] U.S. Cl. ........................................ 435/239; 424/89
[58] Field of Search ............................ 435/239; 424/89

[56] References Cited

U.S. PATENT DOCUMENTS

3,514,374  5/1970  McAleer et al. ................. 435/239
3,547,779  12/1970  Machlowitz et al. ............ 435/239

*Primary Examiner*—Sam Rosen

*Attorney, Agent, or Firm*—Shoemaker and Mattare, Ltd.

[57] ABSTRACT

A-influenza sub-unit vaccine is provided free from contaminants from A-influenza virus-containing allantoic fluid by a combination of selective membrane filtration and chemical splitting of the virus. The allantoic fluid first is freed of undesired particulate matter dimensioned smaller and larger than the virus and also of undesired dissolved matter. The virus then is chemically treated to split off the HA and NA units. Thereafter, the residual virus body, undesired particulates of same particle size as the virus, and a surfactant used in the chemical treatment are eliminated by selective membrane filtration. The procedure is much less costly and simpler to effect than prior art procedures.

7 Claims, No Drawings

PURIFICATION OF INFLUENZA SUB-UNIT VACCINE

FIELD OF INVENTION

The present invention relates to the purification of influenza sub-unit vaccine using simple inexpensive techniques.

BACKGROUND OF THE INVENTION

In the influenza virus particle, the genetic material, ribonucleic acid associated with group-specific nucleoprotein, is surrounded by a double membrane consisting of an inner layer of protein and an outer layer of host-derived lipid material. Two glycoproteins, haemagglutinin (HA) and neuraminidase (NA), appear as projections or spikes on the surface of the viral envelope and make up approximately 36% of the total virus. It is well established that these two glycoproteins are the main immunogenic components of the virus and that all other components, including other virus proteins, nucleic acids and lipids, are non-essential for the induction of immunity and yet may lead to undesired side effects and limit to the dosage which can be administered and the level of immunity which can be achieved.

U.S. Pat. No. 4,064,232, assigned to Sandoz Ltd., describes the isolation of the immunogenic components, i.e. the haemagglutinin and neuraminidase, from influenza viruses by selectively solubilizing the components in an aqueous medium with a cationic surfactant and separating the resulting solubilized components from residual sub-viral particles, such as by centrifugation.

The subunit virus has been proposed to be recovered from the aqueous phase by adding treated bio-beads to the aqueous phase, agitating the mixture for about an hour, dialyzing the agitated mixture against a saline solution and then filtering through a straight through sterilizing membrane filter. This procedure is described in U.S. Pat. No. 4,057,626.

Although this latter technique has proved useful in providing purified sub-unit virus vaccines, nevertheless the costs involved are quite high, in that large amounts of highly sophisticated equipment and procedures are necessary, requiring highly skilled and specialized personnel to carry out the process, high capital investments to purchase and build equipment and a large size facility to house the personnel and equipment, high energy use, and high operating costs in the form of chemical, spare parts and filters.

SUMMARY OF INVENTION

The present invention relates to a much simplified technique for obtaining a purified haemagglutinin and neuraminidase vaccine, using simple membrane filtration techniques. The invention is broadly applicable to any virus having the antigen-producing protein attached in a hydrophobic/hydrophilic manner to the remainder of the virus. For convenience, however, the invention will be described in detail with reference to type A influenza virus but the principles thereof are applicable to any other virus having the above-noted characteristics, such as A1, A2 or B-influenza viruses.

In accordance with the present invention, there is provided a process for the formation of a purified antigen-producing viral sub-unit which is attached to a virus in hydrophobic/hydrophilic manner, which comprises selectively solubilizing the viral sub-unit from the virus, and subjecting the resulting fluid to selective membrane filtration to separate the viral sub-unit from the remainder of the components thereof.

GENERAL DESCRIPTION OF INVENTION AND DESCRIPTION OF PREFERRED EMBODIMENT

The influenza virus to be treated is first propagated in a suitable host media, including mammals, such as, mice, hamsters, ferrets, mink, swine or monkeys; various tissue cultures, such as, those prepared from monkey, calf or hamster kidney cells, and cultures prepared from various embryonic tissues, such as, from chick and duck embryo or from human embryonic lung tissue. The live chick embryo is a particularly susceptible and useful host for the replication of A-influenza virus.

In a conventional procedure, 9 to 12-day old embryonated chicken eggs are pre-candled to eliminate spoiled and non-fertilized eggs and the remaining eggs are then innoculated in the amniotic or allantoic cavity with the particular strain of live A-influenza virus for which a vaccine is to be prepared.

The eggs are incubated at a temperature of about 32° to about 37° C. for a period of two or three days during which the virus rapidly multiplies, following which the eggs are post-candled to eliminate eggs which spoiled or died during the incubation period. The eggs next are refrigerated at a temperature of about 5° C. for a period of approximately 24 hours in order to attenuate the live virus before the egg fluids are aseptically harvested. The allantoic fluid so harvested contains a high concentration of live A-influenza virus.

The A-influenza virus structure is approximately 80 to 120 nanometer in size and 5 to $5.5 \times 10^6$ Daltons in weight. The viral structure, sub-structures and functions are as follows:

(a) Haemagglutinin (HA units) make up 28% of the virus with physical characteristics of weight, 210,000 Daltons, and size and shape, 14 nanometer long triangular rod of 4 nanometer width. HA units are located on the perimeter of the virus body attached to a lipid by-layer through a hydrophobic bond at the end of the HA rod;

(b) Neuraminidase (NA units) make up 8% of the virus with physical characteristics of weight, 270,000 Daltons, and size and shape, $8.5 \times 5 \times 5$ nanometer cube with a 10 nanometer long rod extending from the centre and terminating in a 4 nanometer diameter knob. The NA units are located on the perimeter of the virus body among the HA units attached to the lipid by-layer through a hydrophobic bond at the NA knob;

(c) Polypeptides of the types in very small proportions distributed among the HA and NA units with a weight of 10,000 and 30,000 Daltons respectively;

(d) Remaining virus structure making up 64% of the virus and consisting of nine distinct segments of polynucleotides, single-stranded RNA with a weight ranging from $10^5$ to $10^6$ Daltons, lipid by-layers encapsulating the RNA, and polymerase, nucleocapside, trace carbon and trace disulphide.

The live A-influenza virus-containing aseptically harvested allantoic fluid also contains a considerable amount of particulate and dissolved materials which are harmful to humans. The allantoic fluid is treated in accordance with this invention to a multistage procedure to form a purified A-influenza sub-unit vaccine which contains only HA and NA units, a carrier therefor and a preservative therefor.

The allantoic fluid which constitutes the starting point for the procedure of the present invention can be considered as containing the following six groups of substances:
(a) desirable A-influenza virus,
(b) undesirable particulate matter in the size range of less than about 60 nanometer,
(c) undesirable particulate matter in the size range of about 60 to about 140 nanometer,
(d) undesirable particulate matter in the size range of greater than about 140 nanometer,
(e) undesirable dissolved solids, and
(f) water.

The process of the invention involves the utilization of physical separation procedures using membrane filtration to eliminate impurities. The process for recovery of HA and NA units from the allantoic fluid essentially involves three steps:
(a) purification of the A-influenza vaccine containing allantoic fluid by selective membrane filtration to eliminate undesirable particulate matter which is smaller or larger than the whole virus and the undesirable dissolved solids;
(b) split the virus with a surfactant to solubilize the HA and NA units from the virus; and
(c) purification of the HA and NA units by selective membrane filtration to eliminate undesirable particulates having the same size as the virus and residual virus body.

The process of the invention is quite simple to operate and highly skilled and specialized personnel are not needed to carry out the process. Energy consumption is low, capital investment is decreased and operating costs also are decreased. The overall production cost of the sub-unit vaccine, therefore, is decreased considerably as compared with the prior art.

The purification of the allantoic fluid is effected by selective membrane filtration. In one preferred embodiment, the fluid is first flowed across the surface of a membrane having a pore size larger than the particulate matter of smaller diameter than the virus and a pore size smaller than the virus. In this way, this particulate matter and also undesirable dissolved matter passes through the membrane, while the virus remains, usually in the form of a concentrate.

The concentrated fluid next is flowed across the surface of a membrane having a pore size larger than the virus but smaller than the particulate matter of larger diameter than the virus. The virus permeates the membrane while the undesirable large diameter particulates remain.

It may be desirable to repeat the initial concentration-purification step to decrease the volume of fluid to eliminate any remaining particulate matter of diameter smaller than the virus and to eliminate any remaining undesirable dissolved material by flowing the permeate across the surface of a membrane of pore size dimensioned as in the first step.

The selective membrane filtration operations used in the purification of the allantoic fluid may be accompanied by dilution and washing operations using a physiological isotonic solution, for example, a buffered sodium chloride solution in order to enhance the separations effected in the filtrations.

The virus splitting step may be effected in any convenient manner using any convenient surfactant, generally, a non-ionic surfactant. Suitable surfactants include aryl ether adducts of ethylene oxide, for example, Triton X-100 (trademark of Eastern Kodak). The virus splitting is conveniently effected at room temperature (about 20° to 25° C.) in a reaction time of about 30 to 60 minutes. The quantity of surfactant used should be sufficient to effect separation of all the HA and NA units from the virus, usually about 1 to about 1.5 wt.% of the surfactant being used.

Once the HA and NA units have been split from the virus, the resulting fluid is subjected to selective membrane filtration to separate the HA and NA units from the remaining solids and the surfactant molecules. This is preferably effected by flowing the fluid across a membrane having a pore size which permits the HA and NA units to pass therethrough but is smaller than the remaining whole virus body and particulate matter having the same size range as the whole virus.

In this way, the HA and NA units pass through the membrane while the solids do not. A final selective filtration eliminates the surfactant by using a membrane through which the HA and NA units cannot permeate but the surfactant molecules may. Repeated washing may be carried out, if desired, to remove the last traces of the surfactant.

Preservatives and adjuvants may be added to the purified sub-unit vaccine, as desired. The vaccines produced in accordance with this invention are useful as vaccines against influenza.

The simple yet unique approach used in this invention utilizes specific physical interaction between specifically pore-sized membranes and the fluids containing matters which must be removed to process A-influenza allantoic fluid to form A-influenza sub-unit vaccine.

The filtration operations effected in the above-described preferred embodiment of the invention may be carried out in any tangential flow type convenient apparatus housing the filter membranes. One suitable piece of equipment is described in my copending United States patent application Serial No. filed , the disclosure of which is incorporated herein by reference.

The process of the present invention is described hereinafter with reference to the following specific example whereby 1000 ml of harvested egg allantoic fluid containing attenuated live A-influenza virus is processed to 100 ml of final purified A-influenza sub-unit vaccine.

EXAMPLE

Step I—reduction of volume of fluid and elimination of the majority of the particulate matter smaller than the virus and the dissolved solids.

1000 ml of allantoic fluid containing A-influenza virus were mixed with 125 ml of 0.006 M solution of influenza phosphate buffered saline and 0.05 wt.% Triton X-100 detergent (an alkylphenoxypolyethoxyethanol) and the mixture was pumped at a rate of 1.8 l/min, 350 millibar and 0.3 meters/sec, using a peristaltic pump, across a 40 $cm^2$, 0.1 micron pore size, type VM membrane by Millipore Corporation. The buffered saline comprised 1 liter of water for injection USP XIX, 8.7 g of sodium chloride, 0.663 g of sodium dibasic phosphate, 0.2 g of sodium monobasic phosphate and hydrochloric acid or sodium hydroxide to pH 7.1 to 7.2.

The concentration-purification operation was continued until the allantoic fluid-saline-detergent mixture volume was decreased to 500 ml at which time a further 1000 ml of the saline and 0.05 wt.% of the detergent were added at a rate equal to the concentration-purification rate in order to wash additional impurities out of the allantoic fluid with the saline and to decrease aggregation of egg protein with the detergent. When the volume of fluid and added saline was reduced to 100 ml of concentrate, this step was terminated.

Step II—elimination of particulate matter larger than the virus and recovery of an optimum of whole virus.

The 100 ml of concentrated allantoic fluid from Step I was pumped at a rate of 1.8 l/min, 350 millibar and 0.3 meters/sec, using a peristaltic pump, across a 40 cm$^2$, 0.45 micron pore size, type HA membrane by Millipore Corporation. 1.6 ml/min of concentrated fluid permeated the membrane to provide a filtered-concentrated-purified whole virus-containing fluid.

250 ml of saline and 0.05 wt.% detergent were added at a rate equal to the permeate rate. The purpose of adding this additional saline and detergent is to wash additional viruses through the membrane with the saline and to decrease aggregation of egg protein with the detergent. When 300 ml of filtered-purified whole virus fluid had permeated the membrane, Step II was terminated.

Step III—decrease in fluid volume and elimination of any remaining particulate matter smaller than the whole virus and dissolved solids.

The 300 ml of filtered-purified-whole virus fluid from Step II was pumped at a rate of 1.8 l/min, 350 millibar and 0.3 meters/sec, using a peristaltic pump, across a 40 cm$^2$, 0.1 micron pore size, type VM membrane by Millipore Corporation. The concentration-purification operation was continued until the whole virus fluid volume was reduced to 150 ml, at which time 200 ml of additional saline was added at a rate equal to the concentration-purification rate, in order to wash additional impurities out of the whole virus fluid. When the volume of the whole virus fluid was decreased to 125 ml, Step III was terminated.

Step IV—separation of HA and NA units from whole virus.

The 125 ml of purified whole virus fluid from Step III were mixed vigorously with 1.25 ml of Triton X-100 without foaming for 45 minutes using a magnetic stirrer. After the stirring, the split virus fluid was settled for 15 minutes.

Step V—elimination of particulate matter having the same size as the whole virus and recovery of an optimum of HA and NA units.

The split virus fluid from Step IV was pumped at a rate of 1.8 l/min, 350 millibar and 0.3 meters/sec, using a peristaltic pump, across a 40 cm$^2$, 0.1 micron pore size, type VM membrane by Millipore Corporation. 2.3 ml/min of split virus fluid permeated the membrane to provide a filtered-split virus fluid containing HA units, NA units, detergent, saline and waste proteins from the whole virus body.

250 ml of saline were added at a rate equal to the permeate rate, in order to wash additional HA and NA units through the membrane. The permeate is collected in a sterile container of 0.2 nanometer pore size air vent, type FG membrane by Millipore Corporation. When 350 ml of filtered-split virus fluid had permeated the membrane, Step V was terminated.

Step VI—decrease in fluid volume and elimination of detergent and undesirable proteins originating from the whole virus.

The 350 ml of filtered-split virus fluid was pumped at a rate of 1.8 l/min, 350 millibar and 0.3 meters/sec, using a peristaltic pump, across 40 cm$^2$, 100,000 NMWL (nominal molecular weight limit) pore size, type PTHK membrane by Millipore Corporation. The concentration-purification operation was continued until the filtered-split virus fluid volume was decreased to 50 ml, at which time 150 ml of saline was added. The concentration and saline addition procedures were repeated six times, at which time the detergent concentration was decreased to 50 ml.

Step VII—addition of preservative and dilution of virus fluid to required HA and NA concentrations.

The 50 ml of purified split virus fluid from Step VI were mixed with 50 ml of saline. Formalin was added to a concentration of 0.01 wt.% and a 10 wt.% solution of thimerosal (sodium ethylmercurithiosalicylate) was added to provide a concentration of 1:20,000. The final product was a 100 ml A-influenza sub-unit vaccine.

SUMMARY OF DISCLOSURE

In summary of this disclosure, the present invention provides an improved procedure for the isolation of pure haemagglutinin and neuraminidase sub-unit vaccine from A-influenza virus-containing allantoic fluid. Modifications are possible within the scope of the invention.

What I claim is:

1. A process for preparing a purified influenza sub-unit vaccine containing haemagglutinin (HA) and neuraminidase (NA) units from influenza virus-containing allantoic fluid which was formed by propagating the virus in a host medium, and which contains particulate matter of size ranges less than, the same as, and greater than the virus, which process comprises:
   (a) subjecting said allantoic fluid to multiple selective membrane filtration to remove from said fluid undesirable dissolved solids and undesirable particulate matter in the size ranges which are less than and greater than the virus,
   (b) selectively solubilizing the HA and NA units from the virus with a surfactant, and
   (c) subjecting the resulting fluid to multiple selective membrane filtration to separate the haemagglutinin (HA) and neuraminidase (NA) from larger particles of virus and particulate matter and then to remove the surfactant from the HA and NA to produce the HA and NA sub-unit vaccine.

2. The process of claim 1 wherein said selective membrane filtration steps are effected by flowing a fluid across the surface of a membrane having critically-dimensioned pores.

3. The process of claim 1 wherein step (a) is effected by:
   (i) flowing said allantoic fluid across the surface of a first membrane having a pore size sufficient to permit the particulate matter of the size range less than the virus and the undesirable dissolved matter to pass therethrough and insufficient to permit the virus to pass therethrough, whereby the undesirable particulate matter of the size range less than the virus and undesirable dissolved matter passes through the membrane and the virus remains in a concentrate, and
   (ii) flowing the concentrate across the surface of a membrane having a pore size sufficient to permit the virus to pass therethrough but insufficient to permit the particulate matter of the size range greater than the virus to pass therethrough, whereby the virus passes through the membrane as a filtrate and the undesirable particulate matter in the size range greater than the virus is prevented from passing through the membrane.

4. The process of claim 3 wherein step (i) is repeated on the filtrate from step (ii), whereby any remaining undesirable dissolved matter and any remaining particulate matter of diameter smaller than the virus are eliminated from the filtrate.

5. The process of claim 3 wherein step (c) is effected by:

(i) flowing the fluid resulting from step (b) across a membrane having a pore size sufficient to permit the HA and NA units to pass therethrough and insufficient to permit the residual virus body and undesirable particulate matter having the same size range as the whole virus to pass therethrough, whereby said HA and NA units pass through the membrane in the form of a filtrate, and (ii) flowing the HA and NA-containing filtrate across a membrane having a pore size insufficient to permit HA and NA units to pass therethrough but sufficient to permit surfactant molecules to pass therethrough, whereby the surfactant molecules pass through the membrane and a purified HA and NA-sub-unit vaccine remains.

6. The process of claim 3, 4 or 5, wherein dilution and washing of the fluid by a physiological isotonic solution is effected during each membrane filtration.

7. The process of claim 1, 2, 3, 4, or 5 wherein said influenza virus is A-influenza virus.

* * * * *